United States Patent
Lee et al.

(10) Patent No.: US 7,416,705 B2
(45) Date of Patent: Aug. 26, 2008

(54) SPOTTING DEVICE FOR MANUFACTURING DNA MICROARRAY AND SPOTTING METHOD USING THE SAME

(75) Inventors: Jeong-gun Lee, Seoul (KR); Hun-joo Lee, Seoul (KR)

(73) Assignee: Samsung Electronics Co., Ltd. (KR)

( * ) Notice: Subject to any disclaimer, the term of this patent is extended or adjusted under 35 U.S.C. 154(b) by 802 days.

(21) Appl. No.: 11/011,017

(22) Filed: Dec. 10, 2004

(65) Prior Publication Data

US 2005/0158755 A1    Jul. 21, 2005

(30) Foreign Application Priority Data

Dec. 24, 2003    (KR)    ............ 10-2003-0096292

(51) Int. Cl.
*B01L 3/02*    (2006.01)
*G01N 1/10*    (2006.01)

(52) U.S. Cl. ............ 422/100; 436/180; 73/663.11; 73/863.32; 73/864.01; 73/864.02; 435/6

(58) Field of Classification Search ........ 422/100; 436/180; 435/6; 73/863.11, 863.32, 864, 73/864.02

See application file for complete search history.

(56) References Cited

U.S. PATENT DOCUMENTS

| | | | |
|---|---|---|---|
| 4,226,266 A | | 10/1980 | Guigan ............ 141/11 |
| 5,798,788 A | * | 8/1998 | Meehan et al. ............ 348/180 |
| 6,309,891 B1 | | 10/2001 | Shalon et al. ............ 436/180 |
| 6,342,184 B1 | * | 1/2002 | Bevan et al. ............ 422/70 |
| 6,911,181 B1 | * | 6/2005 | McNeil ............ 422/100 |
| 6,953,551 B2 | * | 10/2005 | Chen et al. ............ 422/100 |
| 2003/0175827 A1 | * | 9/2003 | Stillman et al. ............ 435/7.9 |
| 2003/0211987 A1 | * | 11/2003 | Labat et al. ............ 514/12 |
| 2006/0094119 A1 | * | 5/2006 | Ismagilov et al. ............ 436/53 |
| 2006/0131196 A1 | * | 6/2006 | Fuhr et al. ............ 206/438 |

FOREIGN PATENT DOCUMENTS

| | | |
|---|---|---|
| DE | 199 64 054 | 7/2001 |
| WO | WO 99/09394 | 2/1999 |

OTHER PUBLICATIONS

European Search Report; Application No. EP 04 02 9349; Date: Mar. 31, 2005.

* cited by examiner

*Primary Examiner*—Brian R. Gordon
(74) *Attorney, Agent, or Firm*—Cantor Colburn LLP (57) ABSTRACT

A spotting device for manufacturing a DNA microarray and a spotting method using the same are provided. The spotting device for dropping and immobilizing a solution of biomolecules, for example nucleic acids such as probe DNA, mRNA, and peptide nucleic acid (PNA), and proteins on a DNA microarray surface to manufacture a DNA microarray, includes a first microchannel with a tube shape; a supplying unit supplying the solution of biomolecules to the first microchannel; a biomolecule solution droplet forming unit crosslinked to the first microchannel and forming biomolecule solution droplets with a predetermined size by periodically jetting a gas toward the biomolecule solution flowing in the first microchannel; a second microchannel linked to the first microchannel and having a greater diameter than the first microchannel; a cooling unit surrounding at least a part of the second microchannel to freeze the biomolecule solution droplets which pass through the second microchannel; and a spotting unit thawing the frozen biomolecule solution droplets and dropping the thawed biomolecule solution droplets on a surface of the DNA microarray. The spotting device can form spots with uniform shape, minimize an effect of temperature on biomolecules, and easily manipulate biomolecules when manufacturing a DNA microarray.

13 Claims, 7 Drawing Sheets

| SPOT 1: 9862 AU | SPOT 2: 7886 AU | SPOT 3: 842 AU | SPOT 4: 752 AU |
|---|---|---|---|
| SPOT 5: 7637 AU | SPOT 6: 6662 AU | SPOT 7: 668 AU | SPOT 8: 1018 AU |
| SPOT 9: 6891 AU | SPOT 10: 6327 AU | SPOT 11: 732 AU | SPOT 12: 904 AU |
| SPOT 13: 8580 AU | SPOT 14: 13425 AU | SPOT 15: 956 AU | SPOT 16: 958 AU |

FIG. 6C

| SPOT 1: 1540 μm | SPOT 2: 1620 μm | SPOT 3: 1380 μm | SPOT 4: 1600 μm |
|---|---|---|---|
| SPOT 5: 1540 μm | SPOT 6: 1580 μm | SPOT 7: 1460 μm | SPOT 8: 1420 μm |
| SPOT 9: 1620 μm | SPOT 10: 1620 μm | SPOT 11: 1540 μm | SPOT 12: 1540 μm |
| SPOT 13: 1620 μm | SPOT 14: 920 μm | SPOT 15: 960 μm | SPOT 16: 1540 μm |

SPOTTING DEVICE FOR MANUFACTURING DNA MICROARRAY AND SPOTTING METHOD USING THE SAME

BACKGROUND OF THE INVENTION

This application claims the benefit of Korean Patent Application No. 2003-96292, filed on Dec. 24, 2003, in the Korean Intellectual Property Office, the disclosure of which is incorporated herein in its entirety by reference.

1. Field of the Invention

The present invention relates to a spotting device for manufacturing a DNA microarray and a spotting method using the same. More particularly, the present invention relates to a spotting device for dropping and immobilizing a solution of biomolecules, for example, nucleic acids such as probe DNA, mRNA, and peptide nucleic acid (PNA), and proteins on a DNA microarray surface to manufacture a DNA microarray and a spotting method using the same.

2. Description of the Related Art

With progress on the human genome project, a demand for a method to rapidly provide an enormous amount of genetic information with regard to the diagnosis, treatment, and prevention of hereditary diseases has greatly increased. Though a method of Sanger which had been used to analyze a base sequence until that time was steadily progressed by the development of a polymerase chain reaction (PCR) replicating DNA and automation thereof, it could not analyze a large number of genes since an analyzing process was complicated, time consuming, expensive, and high degree of skills were required. Thus, a new system for analyzing a base sequence has been continuously required. According to the needs of the times, there was progress in a manufacturing of a DNA microarray and a technology using the same for last several years.

The "DNA microarray" generally refers to attaching oligonucleotide probes, of which a base sequence is known, having from the minimum several bases to the maximum hundreds of bases to a surface of a solid, such as silicone, surface modified glass, polypropylene, and activated polyacrylamide, at hundreds or one hundred thousands of predetermined positions to microarray. When bonding a target DNA fragment intended to analyze to the DNA microarray, various hybridizations according to a compensatory level between base sequence of the probe attached to the DNA microarray and base sequence of the target DNA fragment occur and are observed and analyzed through an optical method or a radiochemical method to discover the base sequence of the target DNA (sequencing by hybridization; SBH).

A DNA chip manufactured using the DNA microarray can achieve miniaturation of a DNA analysis system, perform a gene analysis using only an ultra trace volume of a sample and examine simultaneously base sequences at various positions on the target DNA. Accordingly, the DNA chip is inexpensive and can rapidly provide genetic information. Also, the DNA chip can simultaneously analyze an enormous amount of genetic information rapidly and clarify the relations between genes, and thus, will be applied to numerous fields, such as the diagnosis of hereditary diseases and cancers, search of a mutant, detection of pathogenic bacteria and fungi, analysis of gene expression, and drug development. Also, the DNA chip can be used in biotech to bring about development. For example, it can be used as a sensor of microorganisms and environmental pollution to find a gene for a material to neutralize poison and gene recombination technology is applied thereto so as to mass produce the material which neutralizes poison or produces crops for medicines and low fat meat.

Figure 1:
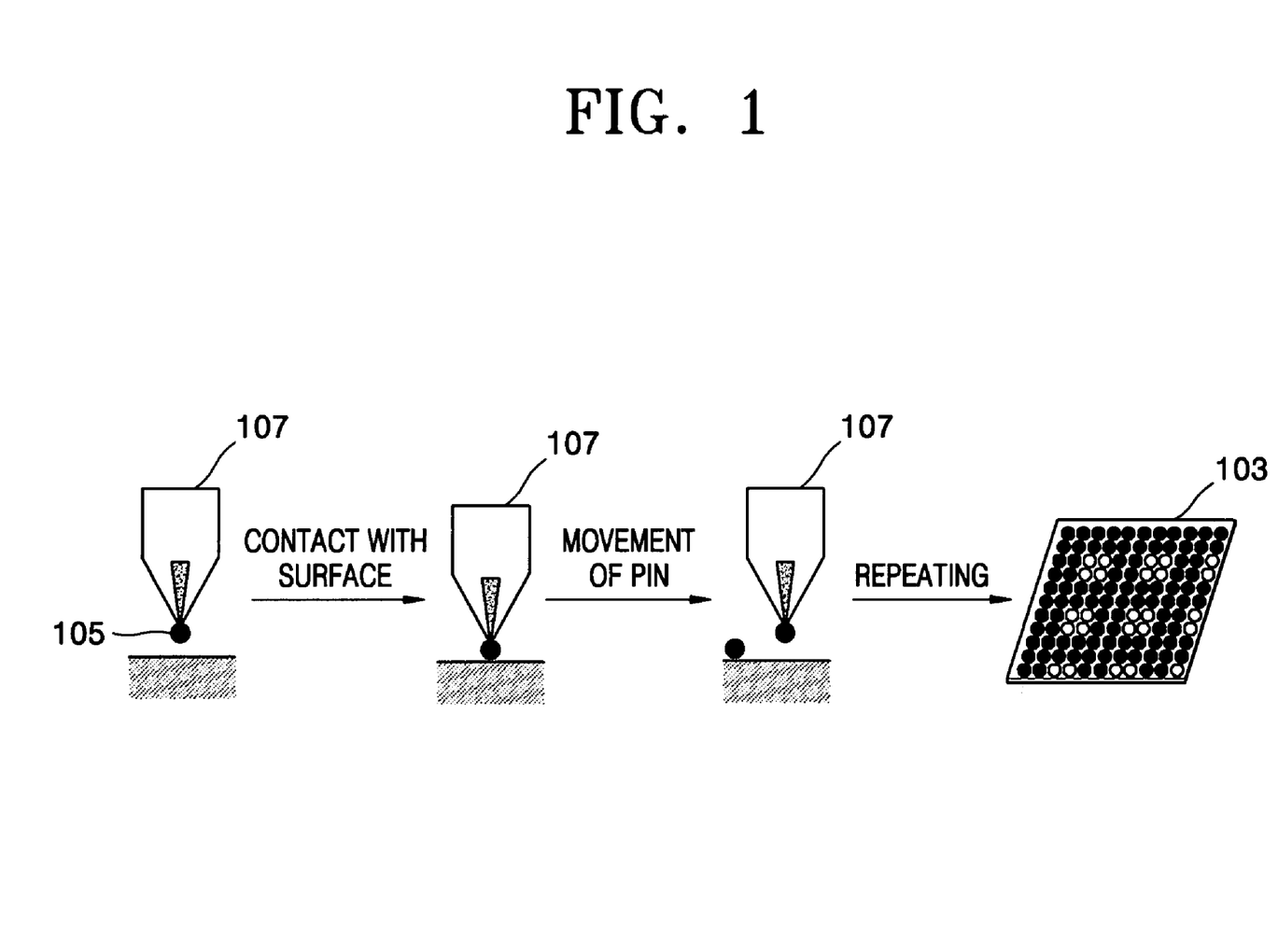
FIG. 1 illustrates a conventional spotting method using a pin for manufacturing a DNA microarray.
Figure 2:
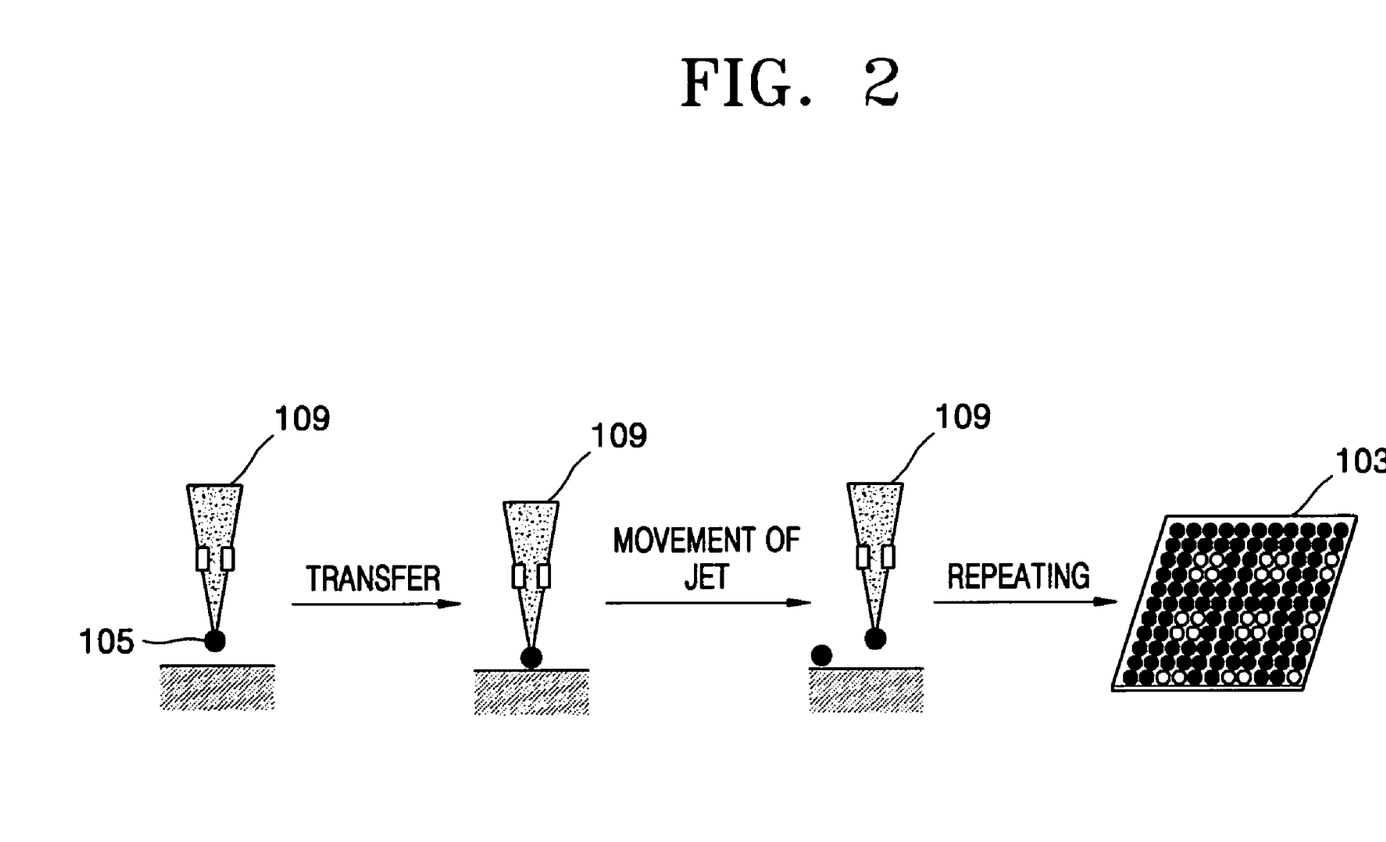
FIG. 2 illustrates a conventional spotting method using inkjet for manufacturing a DNA microarray.

The DNA microarrays may be divided into oligo chips and cDNA chips according to a type of a probe used and may be divided into photolithography chips, spotting chips using a pin, and spotting chips using inkjet according to a manufacturing method. FIGS. 1 and 2 illustrate conventional spotting methods using a pin and inkjet, respectively, for manufacturing a DNA microarray. In the methods, a solution of biomolecules, for example, nucleic acids, such as probe DNA, mRNA, PNA, and proteins, are dropped and immobilized on a DNA microarray surface. All biomolecules used in the methods are in liquid state.

Regarding conventional spotting devices for manufacturing a DNA microarray and spotting methods using the same, in the case of using a pin, since the pin is used to spot a biomolecule solution which is then washed, and then it is used to spot another biomolecule solution, 99% or more of a biomolecule solution is discarded without being used. Also, the sizes of spots are not uniform, the pin is occasionally clogged, life time of the pin is not long, the concentration of the biomolecule solution is varied according to spotting time, and long time is required for spotting the biomolecule solution. In the case of using inkjet, a bubble jet method momentarily requires ultrahigh heat, and thus, a part of the biomolecules which are sensitive to heat may be affected by the heat. Also, a nozzle is occasionally clogged.

SUMMARY OF THE INVENTION

The present invention provides a spotting device which can produce spots with more uniform shapes than a conventional spotting device when manufacturing biochips or DNA microarrays, minimize an effect of temperature on biomolecules, and easily manipulate biomolecules, and a spotting method using the same.

The present invention also provides a spotting device capable of significantly reducing a time required for manufacturing biochips or DNA microarrays and a spotting method using the same.

According to an aspect of the present invention, there is provided a spotting device for dropping and immobilizing a solution of biomolecules, for example, nucleic acids such as probe DNA, mRNA, and peptide nucleic acid (PNA), and proteins on a DNA microarray surface to manufacture a DNA microarray, the spotting device including: a first microchannel with a tube shape; a supplying unit supplying the solution of biomolecules to the first microchannel; a biomolecule solution droplet forming unit cross-linked to the first microchannel and forming biomolecule solution droplets with a predetermined size by periodically jetting a gas toward the biomolecule solution flowing in the first microchannel; a second microchannel linked to the first microchannel and having a greater diameter than the first microchannel; a cooling unit surrounding at least a part of the second microchannel to freeze the biomolecule solution droplets passing through the second microchannel; and a spotting unit dropping the frozen biomolecule solution droplets on the DNA microarray surface.

The spotting unit includes: a third microchannel having a microvalve opening and closing a path which the frozen biomolecule solution droplets pass through, and storing the frozen biomolecule solution droplets at sub-zero temperatures; a discharger coupled to the third microchannel and opening the microvalve to discharge the frozen biomolecule solution droplets from the third microchannel; and a fourth microchannel linked to the third microchannel and heated to a predetermined temperature by a heater to thaw the frozen biomolecule solution droplets which have been discharged from the third microchannel.

The predetermined temperature is 20 to 200° C., and the sub-zero temperature is −5 to −30° C. Generally, an adiabatic channel is installed between the third microchannel and the fourth microchannel so as to prevent heat from being conducted from the fourth microchannel to the third microchannel.

Also, the discharger is a microactuator installed over the third microchannel and a plurality of the spotting units may be regularly arranged to reduce a manufacturing time.

The supplying unit includes a solution reservoir linked to the first microchannel to store the biomolecule solution; and a first micropump which pumps the biomolecule solution stored in the solution reservoir into the first microchannel.

Also, the gas is air and the biomolecule solution droplet forming unit includes an air reservoir to store air and a second micropump periodically jetting the air stored in the air reservoir toward the biomolecule solution flowing in the first microchannel.

The predetermined size of the biomolecule solution droplets may be a diameter of 2000 μm to 1 nm.

Also, the cooling unit may further include a frozen biomolecule solution droplet reservoir to store the frozen biomolecule solution droplets.

According to another aspect of the present invention, there is provided a spotting method for dropping and immobilizing a solution of biomolecules, for example, nucleic acids such as probe DNA, mRNA, and peptide nucleic acid (PNA), and proteins on a DNA microarray surface to manufacture a DNA microarray, the spotting method including: (a) allowing the biomolecule solution to flow in a first microchannel with a tube shape; (b) periodically jetting a gas toward the biomolecule solution flowing in the first microchannel to form biomolecule solution droplets with a predetermined size; (c) freezing the biomolecule solution droplets passing through a second microchannel linked to the first microchannel and having a greater diameter than the first microchannel to store the frozen biomolecule solution droplets; and (d) thawing the frozen biomolecule solution droplets and dropping the thawed biomolecule solution droplets on the DNA microarray surface.

In the operation (c), the storage of the frozen biomolecule solution droplets may be accomplished in a third microchannel maintained at −5 to −30° C.

In the operation (d), the frozen biomolecule solution droplets are thawed while passing through a fourth microchannel maintained at 20 to 200° C. by a heater and linked to the third microchannel.

In the operation (b), the gas is air and the predetermined size of the droplets is generally a diameter of 2000 μm to 1 nm.

In the operation (d), the frozen biomolecule solution droplets may be simultaneously discharged by a plurality of the spotting units regularly arranged, thereby reducing a time for manufacturing the DNA microarray.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings in which embodiments of the invention are shown.

Figure 3:
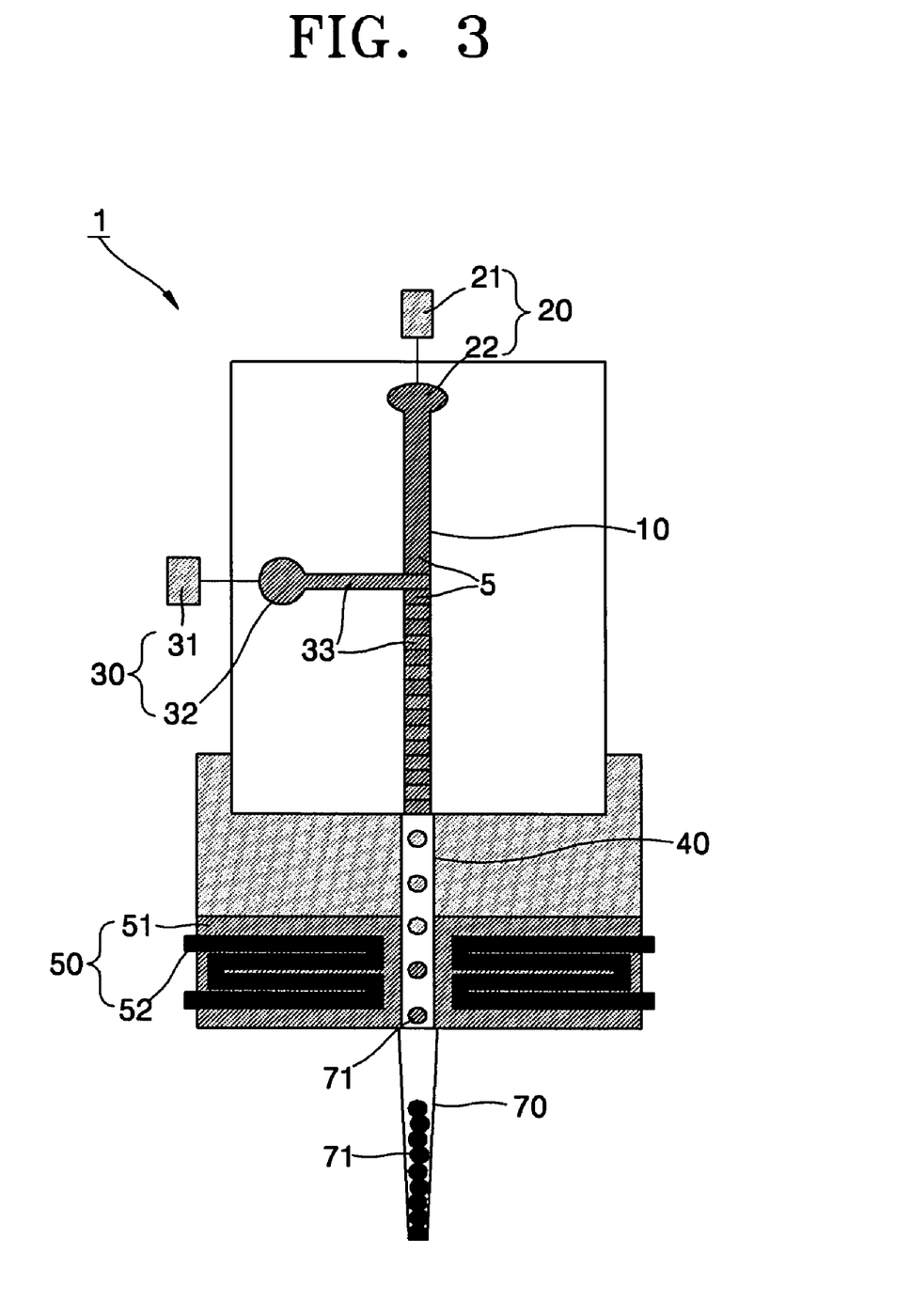
FIG. 3 illustrates a spotting device for manufacturing a DNA microarray according to an embodiment of the present invention for describing a freezing process of a biomolecule solution.
Figure 4:
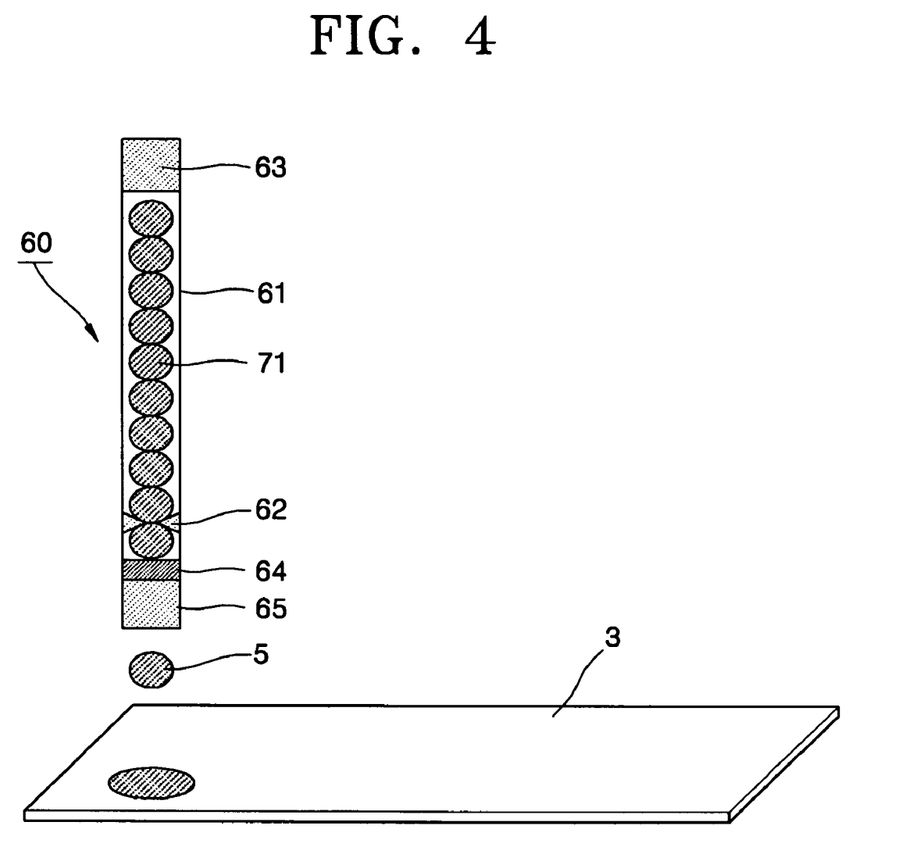
FIG. 4 is a schematic cross-sectional view of a spotting unit of the spotting device illustrated in FIG. 3.

FIG. 3 is a diagram of a spotting device for manufacturing a DNA microarray according to an embodiment of the present invention for describing a freezing process of a biomolecule solution and FIG. 4 is a schematic cross-sectional view of a spotting unit in the spotting device of FIG. 4. As illustrated in FIGS. 3 and 4, the spotting device 1 for manufacturing a DNA microarray 3 according to an embodiment of the present invention includes: a first microchannel 10 with a tube shape; a supplying unit 20 supplying a biomolecule solution 5, for example, nucleic acids such as probe DNA, mRNA, and peptide nucleic acid (PNA), and proteins to the first microchannel 10; a biomolecule solution droplet forming unit 30 cross-linked to the first microchannel 10 and forming biomolecule solution 5 droplets with a predetermined size, generally diameter of 2000 μm to 1 nm by periodically jetting a gas toward the biomolecule solution 5 flowing in the first microchannel 10; a second microchannel 40 linked to the first microchannel 10 and having a greater diameter than the first microchannel 10; a cooling unit 50 surrounding at least a part of the second microchannel 40 to freeze the biomolecule solution 5 droplets passing through the second microchannel 40; and a spotting unit 60 thawing the frozen biomolecule solution droplets 71 and dropping the thawed biomolecule solution droplets on a surface of the DNA microarray 3. Also, a frozen biomolecule solution droplet reservoir 70 storing the biomolecule solution droplets 71 frozen in the cooling unit 50 is separately provided.

The supplying unit 20 supplying the biomolecule solution 5 to the first microchannel 10 includes a solution reservoir 22 linked to the first microchannel 10 and storing the biomolecule solution 5 and a first micropump 21 which pumps the biomolecule solution 5 stored in the solution reservoir 22 to the first microchannel 10.

The biomolecule solution droplet forming unit 30 corsslinked to the first microchannel 10 includes an air reservoir 32 storing air 33 and a second micropump 31 periodically jetting the air 33 stored in the air reservoir 32 toward the biomolecule solution 5 flowing in the first microchannel 10. If the air 33 is jetted substantially perpendicular to the first microchannel 10 by the diaphragm type second micropump 31, the biomolecule solution 5 flowing in the first microchannel 10 changes into droplets with a predetermined size. Although air is used herein, another proper gas may be used.

The second microchannel 40, which is linked to the first microchannel 10, has a greater diameter than the first microchannel 10. Thus, the biomolecule solution 5 droplets with a predetermined size formed by the air 33 flow in the first microchannel 10 in the state of contacting with an inner surface the first microchannel 10, and then, flow in the second microchannel 40 having a greater inner diameter than the first microchannel 10 in the state of being separated from an inner surface of the second microchannel 40, wherein substantially spherical droplets are formed due to surface tension.

The cooling unit 50 is a cryogenic device and includes a cryogenic device body 51 and a cooling tube 52 in which a cryogenic liquid, i.e. liquid low-temperature nitrogen flows. The cooling unit 50 surrounds a part of the second microchannel 40 to freeze the biomolecule solution droplets which pass through the second microchannle 40.

A process of uniformly and finely freezing the biomolecule solution droplets using the spotting device with such construction is as follows. The biomolecule solution 5 is injected to the first microchannel 10 from the solution reservoir 22 by the first micropump 21. The air 33 contained in the air reservoir 32 is periodically injected into the first microchannel 10 in a substantially perpendicular direction using the diaphragm type second micropump 31. The droplet size of the biomolecule solution 5 is determined according to the injection rate of the air 33. That is, if the air 33 is injected fast, small droplets of the biomolecule solution 5 are formed, and if the air 33 is slowly injected, large droplets of the biomolecule solution 5 are formed. Also, the droplet size of the biomolecule solution 5 may vary according to the flow rate of the biomolecule solution 5. That is, if the biomolecule solution 5 flows fast, large droplets of the biomolecule solution 5 are formed, and if the biomolecule solution 5 flows slowly, small droplets of the biomolecule solution 5 are formed. Therefore, by controlling the injection rate of the air 33 and the flow rate of the biomolecule solution 5, the droplets of the biomolecule solution 5 with a desired size can be formed. The formed droplets of the biomolecule solution 5 have a substantially spherical shape while passing through the second microchannel 40. Then, the droplets of the biomolecule solution 5 are frozen while passing through the second microchannel 40 maintained at a low temperature by the cooling unit 50 in which cryogenic liquid such as liquid low temperature nitrogen flows. The frozen biomolecule solution droplets 71 are stored in the frozen biomolecule solution droplet reservoir 70.

The spotting unit 60 includes a third microchannel 61 storing the frozen biomolecule solution droplets and maintained at sub-zero temperatures of about −5 to −30° C.; a discharger 63 coupled to the third microchannel 61 to discharge the frozen biomolecule solution droplets 71 from the third microchannel 61; a fourth microchannel 65 heated to 20-200° C. by a heater to thaw the biomolecule solution droplets 71, which has been discharged from the third microchannel 61; and an adiabatic channel 64 installed between the third microchannel 61 and the fourth microchannel 65 so as to prevent heat from being conducted from the fourth microchannel 65 to the third microchannel 61. A microvalve 62 opening and closing a path which the frozen biomolecule solution droplets 71 pass through is installed in the third microchannel 61. The discharger 63 is a microactuator placed over the third microchannel 61 and may be operated by a mechanical method, piezo method, or an electric field inducing method.

The biomolecule solution droplets 71 which have been frozen in the cooling unit 50 and stored in the frozen biomolecule solution droplet reservoir 70 are then stored in the third microchannel 61. When the microvalve 62 is opened by a microactuator, the frozen biomolecule solution droplets 71, which have been stored in the third microchannel 61, isolated one after another and discharged toward outside. The discharged biomolecule solution droplets are thawed while passing through the fourth microchannel 65 containing a heater. Then, the liquid biomolecule solution droplets are dropped on a surface of a biochip or DNA microarray 3 and the dropped biomolecule solution droplets are immobilized and biomoleculated on the surface of the biochip or DNA microarray 3, thereby completing a spotting process for manufacturing the DNA microarray 3. When a number of spotting units 60 are regularly arranged and thereby several biomolecule solution droplets are simultaneously dropped and immobilized on the biochip or DNA microarray 3, a time required for the spotting process can be significantly reduced.

Examples of a spotting operation using a spotting device for manufacturing a DNA microarray according to an embodiment of the present invention will now be described in more detail with reference to FIGS. 5A and 5B and FIGS. 6A through 6C.

EXAMPLES

Conditions of a spotting experiment were as follows.

Figure 5A:
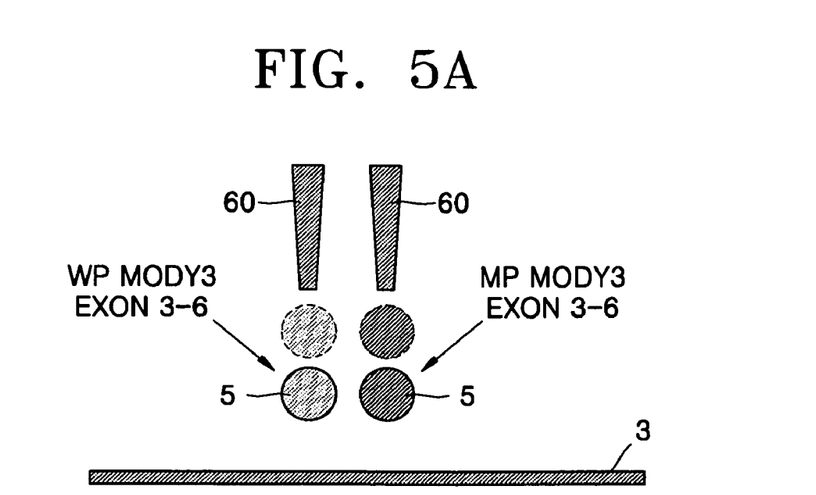
FIGS. 5A and 5B are diagrams for describing a process conducting a spotting experiment using the spotting device illustrated in FIG. 3.
Figure 5B:
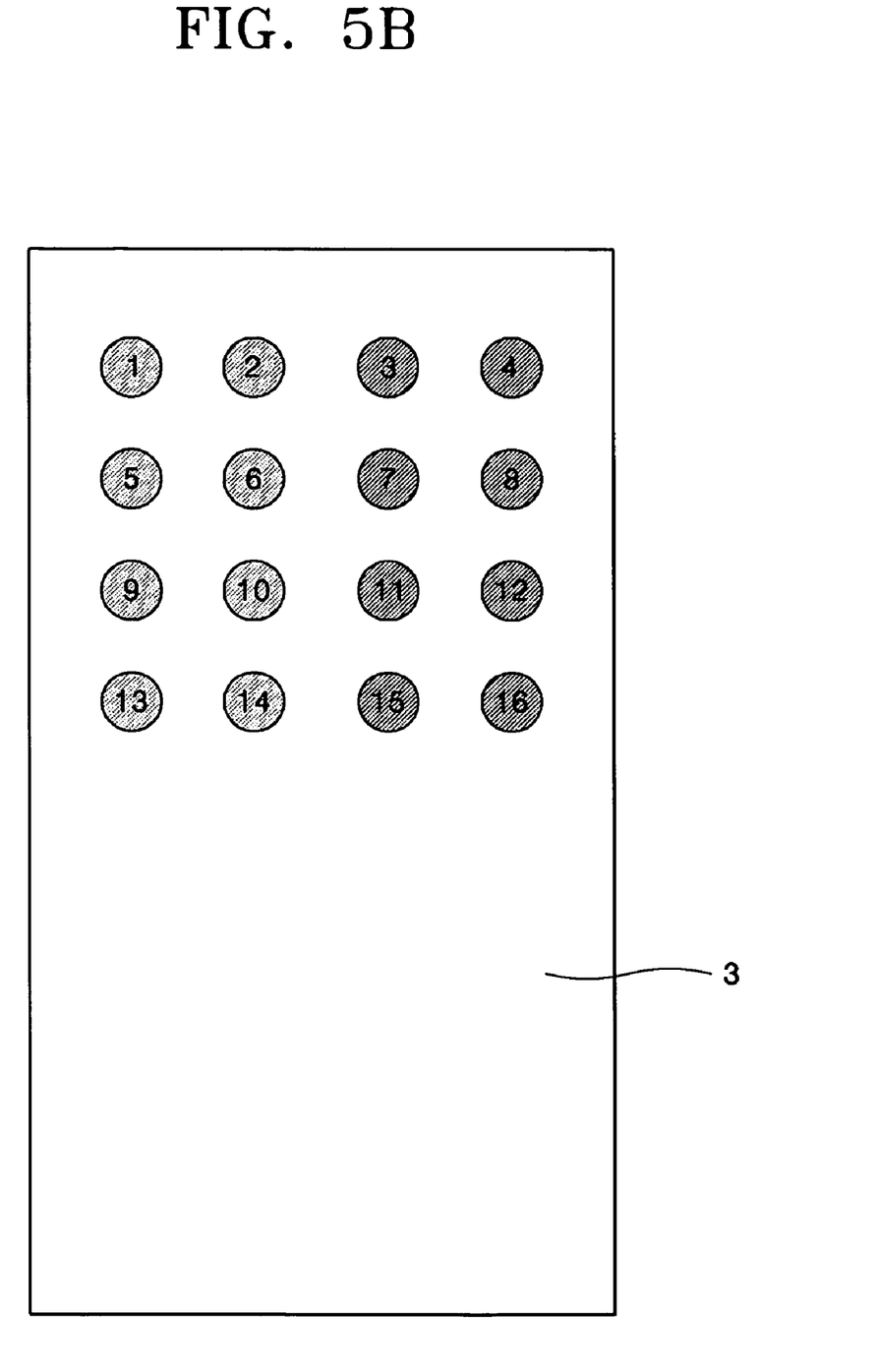

First, probe DNA oligomers were prepared. In FIG. 5B, perfectly matched probe DNA oligomers (WP MODY3 EXON 3-6, $C6NH^2$-5'-CGGAGGAACCGTTTC-3') were assigned to 1, 2, 5, 6, 9, 10, 13, and 14, and mismatched probe DNA oligomers (MP MODY EXON 3-6, $C6NH^2$-5'-CG-GAGGAACCATTTC-3') were assigned to 3, 4, 7, 8, 11, 12, 15, and 16.

Then, 100 uM of the DNA oligomer, 100 uM of PEG, 3 uM of Cy5 activate ester, and a DMSO solution were prepared.

Next, droplets were formed using a spotting device for manufacturing a DNA microarray according to an embodiment of the present invention, frozen at −20° C., and then, subjected to a hybridization using 50 μM Mody3 Exon 3 as a target DNA. At this time, hybridization time was 16 hours and hybridization temperature was 32° C.

After washing, the resultant was scanned using PMT 573 (Scanner GenePix 4000B, Axon instruments, Inc.) at a wavelength of 532 nm in a greenmode.

Figure 6A:
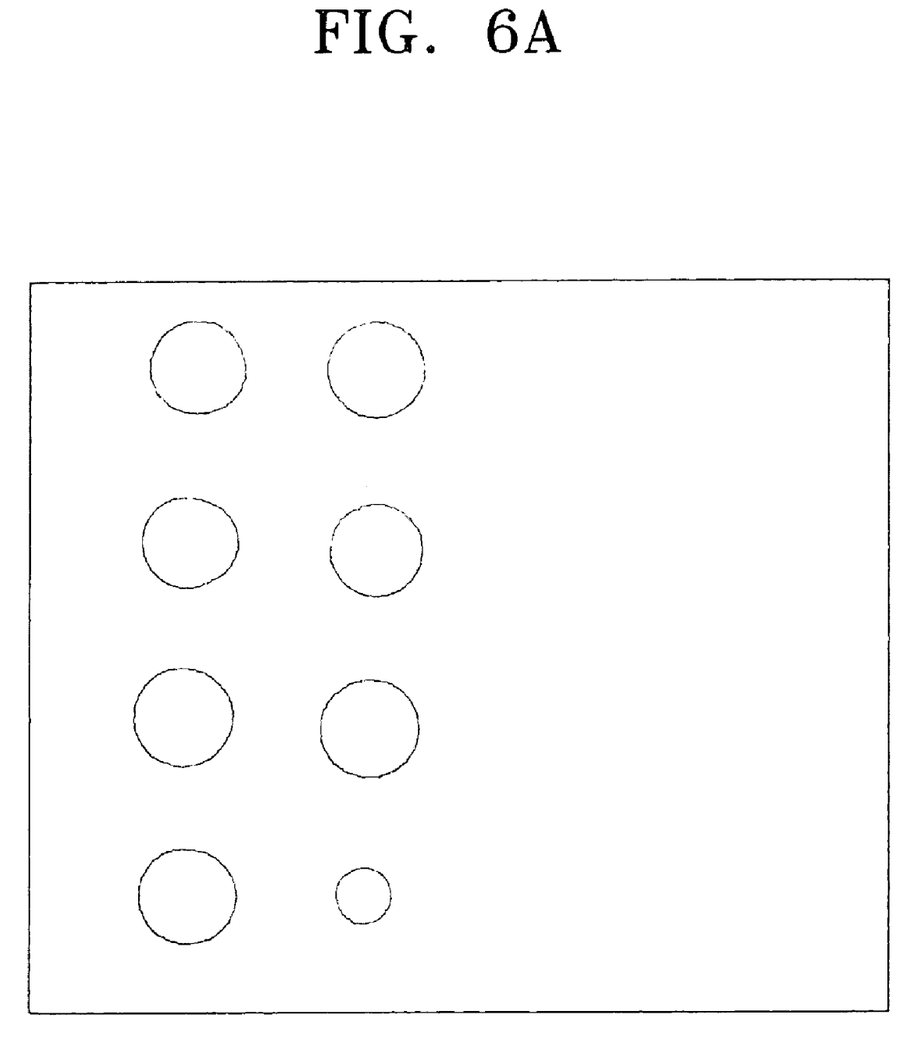
FIGS. 6A through 6C illustrate the experimental results of FIGS. 5A and 5B.
Figure 6B:
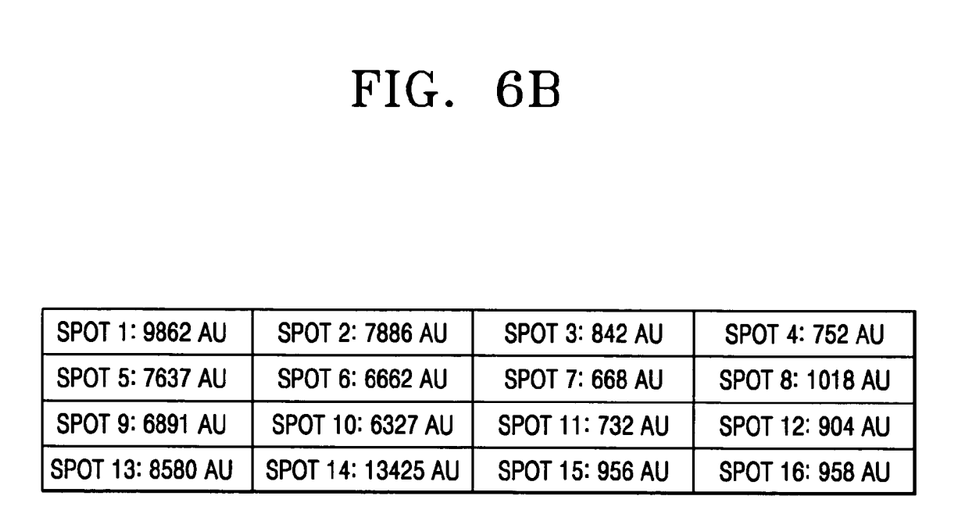
Figure 6C:
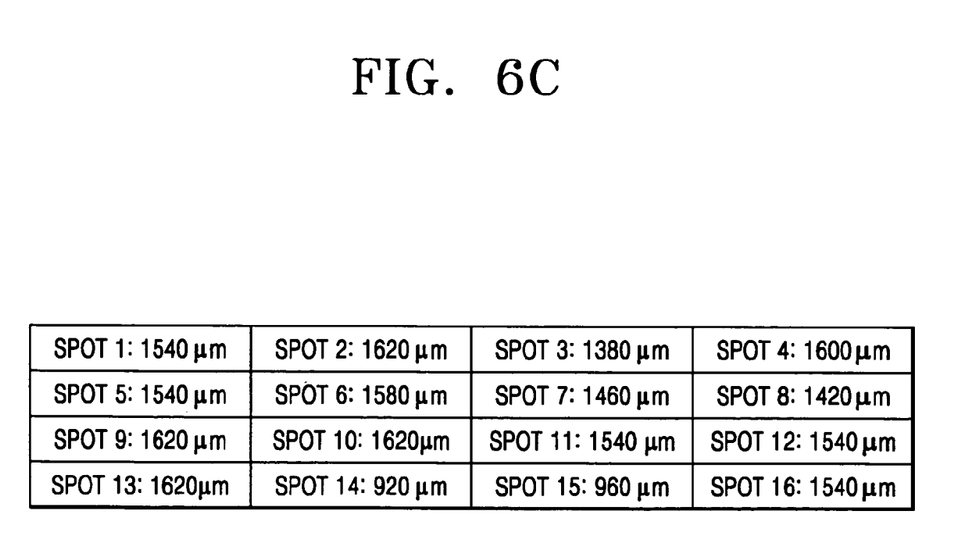

FIG. 6A is a photography of spots after hybridisation and FIGS. 6B and 6C illustrate an intensity and a diameter of the respective spot. As seen from FIGS. 6A through 6C, uniformity of a spot is improved and discriminate ratio is as high as 9.82.

Thus, by using a spotting device including the biomolecule solution droplet forming unit 30 cross-linked to the first microchannel 10 and forming biomolecule solution droplets 5 with a predetermined size by periodically jetting a gas toward the biomolecule solution 5 flowing in the first microchannel 10; the second microchannel 40 linked to the first microchannel 10 and having a greater diameter than the first microchannel 10; the cooling unit 50 surrounding at least a part of the second microchannel 40 to freeze the biomolecule solution 5 droplets passing through the second microchannel 40; and the spotting unit 60 thawing the biomolecule solution droplets 71 and dropping the thawed biomolecule solution droplet on a surface of the DNA microarray 3, when manufacturing a biochip or DNA microarray, spots with a uniform shape can be formed, an effect of temperature on the biomolecule can be minimized, and the biomolecules can be easily manipulated.

Although it is described above that the frozen biomolecule solution droplets 71 are thawed in the fourth microchannel 65 of the spotting unit 60, the frozen biomolecule solution droplet 71 may be thawed in the outside.

Also, although it is described above that the frozen biomolecule solution droplet reservoir 70 storing the frozen biomolecule solution droplet is installed, when the spotting unit 60 is linked to the second microchannel 40, the third microchannel 61 of the spotting unit 60 may function as the frozen biomolecule solution droplet reservoir 70, which eliminates the need for the frozen biomolecule solution droplet reservoir 70.

As described above, according to the present invention, a spotting device capable of forming spots with uniform shape, minimizing an effect of temperature on biomolecules, and easily manipulating biomolecules when manufacturing a biochip or DNA microarray and a spotting method using the same are provided.

Also, a number of spotting units are regularly arranged and a number of biomolecule solution droplets are simultaneously discharged through them, so that the time required for manufacturing a biochip or DNA microarray can be significantly reduced.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A spotting device for dropping and immobilizing a solution of biomolecules, for example, nucleic acids such as probe DNA, mRNA, and peptide nucleic acid (PNA), and proteins on a DNA microarray surface to manufacture a DNA microarray, the spotting device including:
    a first microchannel with a tube shape;
    a supplying unit supplying the solution of biomolecules to the first microchannel;
    a biomolecule solution droplet forming unit cross-linked to the first microchannel and forming biomolecule solution droplets with a predetermined size by periodically jetting a gas toward the biomolecule solution flowing in the first microchannel;
    a second microchannel linked to the first microchannel and having a greater diameter than the first microchannel;
    a cooling unit surrounding at least a part of the second microchannel to freeze the biomolecule solution droplets which pass through the second microchannel; and
    a spotting unit to thaw the biomolecule solution droplets and dropping the thawed biomolecule solution droplets on a surface of the DNA microarray.

2. The spotting device of claim 1, wherein the spotting unit includes:
    a third microchannel having a microvalve opening and closing a path which the frozen biomolecule solution droplets pass through, and storing the frozen biomolecule solution droplets at a sub-zero temperature;
    a discharger coupled to the third microchannel and opening the microvalve to discharge the frozen biomolecule solution droplets from the third microchannel; and
    a fourth microchannel linked to the third microchannel and heated to a predetermined temperature by a heater to thaw the biomolecule solution droplets which have been discharged from the third microchannel.

3. The spotting device of claim 2, wherein the predetermined temperature is 20 to 200° C., the sub-zero temperature is −5 to −30° C., and an adiabatic channel is installed between the third microchannel and the fourth microchannel so as to prevent heat from being conducted from the fourth microchannel to the third microchannel.

4. The spotting device of claim 2, wherein the discharger is a microactuator installed over the third microchannel and a plurality of the spotting units are regularly arranged.

5. The spotting device of claim 1, wherein the supplying unit includes:
    a solution reservoir linked to the first microchannel and storing the biomolecule solution; and
    a first micropump to pump the biomolecule solution stored in the solution reservoir into the first microchannel.

6. The spotting device of claim 1, wherein the gas is air and the biomolecule solution droplet forming unit includes:
    an air reservoir storing air; and
    a second micropump periodically jetting the air stored in the air reservoir toward the biomolecule solution flowing in the first microchannel.

7. The spotting device of claim 1, wherein the predetermined size of the biomolecule solution droplet is a diameter of 2000 μm to 1 nm.

8. The spotting device of claim 1, wherein the cooling unit further includes a frozen biomolecule solution droplet reservoir which stores the frozen biomolecule solution droplets.

9. A spotting method for dropping and immobilizing a solution of biomolecules, for example, nucleic acids such as probe DNA, mRNA, and peptide nucleic acid (PNA), and proteins on a DNA microarray surface to manufacture a DNA microarray, the spotting method including:
    (a) allowing the biomolecule solution to flow in a first microchannel with a tube shape;
    (b) periodically jetting a gas toward the biomolecule solution flowing in the first microchannel to form biomolecule solution droplets with a predetermined size;
    (c) freezing the biomolecule solution droplets passing through a second microchannel linked to the first microchannel and having a greater diameter than the first microchannel and storing the frozen biomolecule solution droplets; and
    (d) thawing the biomolecule solution droplets and dropping the thawed biomolecule solution droplets on the DNA microarray surface.

10. The spotting method of claim 9, wherein in the operation (c), the storage of the frozen biomolecule solution droplets is accomplished in a third microchannel maintained at −5 to −30° C.

11. The spotting method of claim 10, wherein in the operation (d), the frozen biomolecule solution droplets is thawed while being passed through a fourth microchannel maintained at a temperature of 20 to 200° C. by a heater and linked to the third microchannel.

12. The spotting method of claim 9, wherein in the operation (b), the gas is air and the predetermined size is a diameter of 2000 μm to 1 nm.

13. The spotting method of claim 9, wherein in the operation (d), the frozen biomolecule solution droplets are simultaneously discharged by a plurality of the spotting units regularly arranged.

* * * * *